United States Patent
Lowe

(10) Patent No.: US 7,174,636 B2
(45) Date of Patent: Feb. 13, 2007

(54) METHOD OF MAKING AN EMBOLIC FILTER

(75) Inventor: Brian J. Lowe, Zimmerman, MN (US)

(73) Assignee: Scimed Life Systems, Inc., Maple Grove, MN (US)

(*) Notice: Subject to any disclaimer, the term of this patent is extended or adjusted under 35 U.S.C. 154(b) by 656 days.

(21) Appl. No.: 10/234,771

(22) Filed: Sep. 4, 2002

(65) Prior Publication Data

US 2004/0044360 A1   Mar. 4, 2004

(51) Int. Cl.
| | |
|---|---|
| B23P 15/00 | (2006.01) |
| A61M 31/00 | (2006.01) |
| B28B 19/00 | (2006.01) |
| B29C 45/14 | (2006.01) |
| B01D 29/00 | (2006.01) |
| B01D 39/00 | (2006.01) |

(52) U.S. Cl. .............. 29/896.62; 29/428; 29/527.1; 264/239; 264/259; 606/200; 210/767; 210/483; 210/241

(58) Field of Classification Search .............. 29/428, 29/896.62, 527.1; 264/400, 156, 239, DIG. 19, 264/DIG. 48, 259; 606/200, 159; 210/767, 210/483, 241, 499
See application file for complete search history.

(56) References Cited

U.S. PATENT DOCUMENTS

| | | | |
|---|---|---|---|
| 2,868,206 A * | 1/1959 | Stoesser | ............ 606/159 |
| 3,472,230 A | 10/1969 | Fogarty | |
| 3,952,747 A | 4/1976 | Kimmell, Jr. | |
| 3,996,938 A | 12/1976 | Clark, III | |
| 4,046,150 A | 9/1977 | Schwartz et al. | |
| 4,425,908 A | 1/1984 | Simon | |
| 4,590,938 A | 5/1986 | Segura et al. | |
| 4,619,246 A | 10/1986 | Molgaard-Nielsen et al. | |
| 4,650,466 A | 3/1987 | Luther | |
| 4,706,671 A | 11/1987 | Weinrib | |
| 4,723,549 A | 2/1988 | Wholey et al. | |
| 4,790,812 A | 12/1988 | Hawkins, Jr. et al. | |
| 4,790,813 A | 12/1988 | Kensey | |
| 4,794,928 A | 1/1989 | Kletschka | |

(Continued)

FOREIGN PATENT DOCUMENTS

DE    28 21 048    7/1980

(Continued)

OTHER PUBLICATIONS

"Atherosclerotic Disease of the Aortic Arch as a Risk Factor of Recurrent Ischemic Stroke," *The New England Journal of Medicine*, pp. 1216-1221 (May 1996).

(Continued)

Primary Examiner—Jermie E. Cozart
(74) Attorney, Agent, or Firm—Crompton, Seager & Tufte LLC

(57) ABSTRACT

Embolic protection filters and methods of making and using such devices are disclosed. An illustrative method of making a device for filtering embolic debris from a body may include the steps of molding a filter assembly that includes a distal tip and a filter portion, forming a plurality of apertures within the filter portion, and coupling a support member to the filter assembly that is adapted to shift the filter portion between a collapsed configuration and an expanded configuration.

15 Claims, 16 Drawing Sheets

U.S. PATENT DOCUMENTS

| | | |
|---|---|---|
| 4,807,626 A | 2/1989 | McGirr |
| 4,873,978 A | 10/1989 | Ginsburg |
| 4,921,478 A | 5/1990 | Solano et al. |
| 4,921,484 A | 5/1990 | Hillstead |
| 4,926,858 A | 5/1990 | Gifford, III et al. |
| 4,969,891 A | 11/1990 | Gewertz |
| 4,998,539 A | 3/1991 | Delsanti |
| 5,002,560 A | 3/1991 | Machold et al. |
| 5,011,488 A | 4/1991 | Ginsburg |
| 5,053,008 A | 10/1991 | Bajaj |
| 5,071,407 A | 12/1991 | Termin et al. |
| 5,100,423 A | 3/1992 | Fearnot |
| 5,102,415 A | 4/1992 | Guenther et al. |
| 5,133,733 A | 7/1992 | Rasmussen et al. |
| 5,152,771 A | 10/1992 | Sabbaghian et al. |
| 5,152,777 A | 10/1992 | Goldberg et al. |
| 5,160,342 A | 11/1992 | Reger et al. |
| 5,224,953 A | 7/1993 | Morgentaler |
| 5,329,942 A | 7/1994 | Gunther et al. |
| 5,330,484 A | 7/1994 | Gunther |
| 5,354,310 A | 10/1994 | Garnie et al. |
| 5,376,100 A | 12/1994 | Lefebvre |
| 5,421,832 A | 6/1995 | Lefebvre |
| 5,423,742 A | 6/1995 | Theron |
| 5,449,372 A | 9/1995 | Schmaltz et al. |
| 4,842,579 A | 10/1995 | Shiber |
| 5,456,667 A | 10/1995 | Ham et al. |
| 5,462,529 A | 10/1995 | Simpson et al. |
| 5,536,242 A | 7/1996 | Willard et al. |
| 5,549,626 A | 8/1996 | Miller et al. |
| 5,658,296 A | 8/1997 | Bates et al. |
| 5,662,671 A | 9/1997 | Barbut et al. |
| 5,695,519 A | 12/1997 | Summers et al. |
| 5,720,764 A | 2/1998 | Naderlinger |
| 5,728,066 A | 3/1998 | Daneshvar |
| 5,749,848 A | 5/1998 | Jang et al. |
| 5,769,816 A | 6/1998 | Barbut et al. |
| 5,779,716 A | 7/1998 | Cano et al. |
| 5,792,157 A | 8/1998 | Mische et al. |
| 5,795,322 A | 8/1998 | Bouewijn |
| 5,800,457 A | 9/1998 | Gelbfish |
| 5,800,525 A | 9/1998 | Bachinski et al. |
| 5,810,874 A | 9/1998 | Lefebvre |
| 5,814,064 A | 9/1998 | Daniel et al. |
| 5,827,324 A | 10/1998 | Cassell et al. |
| 5,833,644 A | 11/1998 | Zadno-Azizi et al. |
| 5,833,650 A | 11/1998 | Imran |
| 5,846,260 A | 12/1998 | Maahs |
| 5,848,964 A | 12/1998 | Samuels |
| 5,876,367 A | 3/1999 | Kaganov et al. |
| 5,895,399 A | 4/1999 | Barbut et al. |
| 5,910,154 A | 6/1999 | Tsugita et al. |
| 5,911,734 A | 6/1999 | Tsugita et al. |
| 5,925,016 A | 7/1999 | Chornenky et al. |
| 5,925,060 A | 7/1999 | Forber |
| 5,925,062 A | 7/1999 | Purdy |
| 5,935,139 A | 8/1999 | Bates |
| 5,941,869 A | 8/1999 | Patterson et al. |
| 5,941,896 A | 8/1999 | Kerr |
| 5,947,995 A | 9/1999 | Samuels |
| 5,954,745 A | 9/1999 | Gertler et al. |
| 5,980,555 A | 11/1999 | Barbut et al. |
| 5,989,281 A | 11/1999 | Barbut et al. |
| 5,993,469 A | 11/1999 | McKenzie et al. |
| 5,997,557 A | 12/1999 | Barbut et al. |
| 6,001,118 A | 12/1999 | Daniel et al. |
| 6,007,557 A | 12/1999 | Ambrisco et al. |
| 6,010,522 A | 1/2000 | Barbut et al. |
| 6,013,085 A | 1/2000 | Howard |
| 6,027,520 A | 2/2000 | Tsugita et al. |
| 6,042,598 A | 3/2000 | Tsugita et al. |
| 6,051,014 A | 4/2000 | Jang |
| 6,051,015 A | 4/2000 | Maahs |
| 6,053,932 A | 4/2000 | Daniel et al. |
| 6,059,814 A | 5/2000 | Ladd |
| 6,066,149 A | 5/2000 | Samson et al. |
| 6,066,158 A | 5/2000 | Engelson et al. |
| 6,068,645 A | 5/2000 | Tu |
| 6,086,605 A | 7/2000 | Barbut et al. |
| 6,117,154 A | 9/2000 | Barbut et al. |
| 6,129,739 A | 10/2000 | Khosravi |
| 6,136,016 A | 10/2000 | Barbut et al. |
| 6,142,987 A | 11/2000 | Tsugita |
| 6,152,946 A | 11/2000 | Broome et al. |
| 6,165,200 A | 12/2000 | Tsugita et al. |
| 6,168,579 B1 | 1/2001 | Tsugita |
| 6,171,327 B1 | 1/2001 | Daniel et al. |
| 6,171,328 B1 | 1/2001 | Addis |
| 6,179,851 B1 | 1/2001 | Barbut et al. |
| 6,179,859 B1 | 1/2001 | Bates et al. |
| 6,179,861 B1 | 1/2001 | Khosravi et al. |
| 6,203,561 B1 | 3/2001 | Ramee et al. |
| 6,206,868 B1 | 3/2001 | Parodi |
| 6,214,026 B1 | 4/2001 | Lepak et al. |
| 6,221,006 B1 | 4/2001 | Dubrul et al. |
| 6,224,620 B1 | 5/2001 | Maahs |
| 6,231,544 B1 | 5/2001 | Tsugita et al. |
| 6,235,044 B1 | 5/2001 | Root et al. |
| 6,235,045 B1 | 5/2001 | Barbut et al. |
| 6,238,412 B1 | 5/2001 | Dubrul et al. |
| 6,245,087 B1 | 6/2001 | Addis |
| 6,245,088 B1 | 6/2001 | Lowery |
| 6,245,089 B1 | 6/2001 | Daniel et al. |
| 6,258,115 B1 | 7/2001 | Dubrul |
| 6,264,663 B1 | 7/2001 | Cano |
| 6,264,672 B1 | 7/2001 | Fisher |
| 6,270,513 B1 | 8/2001 | Tsugita et al. |
| 6,277,138 B1 | 8/2001 | Levinson et al. |
| 6,277,139 B1 | 8/2001 | Levinson et al. |
| 6,280,413 B1 | 8/2001 | Clark et al. |
| 6,287,321 B1 | 9/2001 | Jang |
| 6,290,710 B1 | 9/2001 | Cryer et al. |
| 6,309,399 B1 | 10/2001 | Barbut et al. |
| 6,319,268 B1 | 11/2001 | Ambrisco et al. |
| 6,344,049 B1 | 2/2002 | Levinson et al. |
| 6,565,591 B2 * | 5/2003 | Brady et al. ............... 606/200 |
| 6,740,061 B1 * | 5/2004 | Oslund et al. ............. 604/104 |
| 6,887,257 B2 * | 5/2005 | Salahieh et al. ........... 606/200 |
| 2002/0072730 A1 | 6/2002 | McGill et al. |

FOREIGN PATENT DOCUMENTS

| | | |
|---|---|---|
| DE | 34 17 738 | 11/1985 |
| DE | 40 30 998 A1 | 10/1990 |
| DE | 199 16 162 | 10/2000 |
| EP | 0 200 688 | 11/1986 |
| EP | 0 293 605 A1 | 12/1988 |
| EP | 0 411 118 A1 | 2/1991 |
| EP | 0 427 429 A2 | 5/1991 |
| EP | 0 437 121 B1 | 7/1991 |
| EP | 0 472 334 A1 | 2/1992 |
| EP | 0 472 368 A2 | 2/1992 |
| EP | 0 533 511 A1 | 3/1993 |
| EP | 0 655 228 A1 | 11/1994 |
| EP | 0 686 379 A2 | 6/1995 |
| EP | 0 696 447 A2 | 2/1996 |
| EP | 0 737 450 A1 | 10/1996 |
| EP | 0 743 046 A1 | 11/1996 |
| EP | 0 759 287 A1 | 2/1997 |
| EP | 0 771 549 A2 | 5/1997 |
| EP | 0 784 988 A1 | 7/1997 |
| EP | 0 852 132 A1 | 7/1998 |
| EP | 1 127 556 A2 | 8/2001 |
| FR | 2 580 504 | 10/1986 |

| | | |
|---|---|---|
| FR | 2 643 250 A1 | 8/1990 |
| FR | 2 666 980 | 3/1992 |
| FR | 2 694 687 | 8/1992 |
| FR | 2 768 326 A1 | 3/1999 |
| GB | 2 020 557 B | 1/1983 |
| JP | 8-187294 A | 7/1996 |
| SU | 764684 | 9/1980 |
| WO | WO 88/09683 | 12/1988 |
| WO | WO 92/03097 | 3/1992 |
| WO | WO 94/14389 | 7/1994 |
| WO | WO 94/24946 | 11/1994 |
| WO | WO 96/01591 | 1/1996 |
| WO | WO 96/10375 | 4/1996 |
| WO | WO 96/19941 | 7/1996 |
| WO | WO 96/23441 | 8/1996 |
| WO | WO 96/33677 | 10/1996 |
| WO | WO 97/17100 | 5/1997 |
| WO | WO 97/27808 | 8/1997 |
| WO | WO 97/42879 | 11/1997 |
| WO | WO 98/02084 | 1/1998 |
| WO | WO 98/02112 | 1/1998 |
| WO | WO 98/23322 | 6/1998 |
| WO | WO 98/33443 | 8/1998 |
| WO | WO 98/34673 | 8/1998 |
| WO | WO 98/36786 | 8/1998 |
| WO | WO 98/38920 | 9/1998 |
| WO | WO 98/38929 | 9/1998 |
| WO | WO 98/39046 | 9/1998 |
| WO | WO 98/39053 | 9/1998 |
| WO | WO 98/46297 | 10/1998 |
| WO | WO 98/47447 | 10/1998 |
| WO | WO 98/49952 | 11/1998 |
| WO | WO 98/50103 | 11/1998 |
| WO | WO 98/51237 | 11/1998 |
| WO | WO 98/55175 | 12/1998 |
| WO | WO 99/09895 | 3/1999 |
| WO | WO 99/22673 | 5/1999 |
| WO | WO 99/23976 | 5/1999 |
| WO | WO 99/25252 | 5/1999 |
| WO | WO 99/30766 | 6/1999 |
| WO | EP 0 934 729 | 8/1999 |
| WO | WO 99/40964 | 8/1999 |
| WO | WO 99/42059 | 8/1999 |
| WO | WO 99/44510 | 9/1999 |
| WO | WO 99/44542 | 9/1999 |
| WO | WO 99/55236 | 11/1999 |
| WO | WO 99/58068 | 11/1999 |
| WO | WO 00/07521 | 2/2000 |
| WO | WO 00/07655 | 2/2000 |
| WO | WO 00/09054 | 2/2000 |
| WO | WO 00/16705 | 3/2000 |
| WO | WO 00/49970 | 8/2000 |
| WO | WO 00/53120 | 9/2000 |
| WO | WO 00/67664 | 11/2000 |
| WO | WO 00/67665 | 11/2000 |
| WO | WO 00/67666 | 11/2000 |
| WO | WO 00/67668 | 11/2000 |
| WO | WO 00/67669 | 11/2000 |
| WO | WO 01/05462 | 1/2001 |
| WO | WO 01/08595 | 2/2001 |
| WO | WO 01/08596 | 2/2001 |
| WO | WO 01/08742 | 2/2001 |
| WO | WO 01/08743 | 2/2001 |
| WO | WO 01/10320 | 2/2001 |
| WO | WO 01/15629 | 3/2001 |
| WO | WO 01/21077 | 3/2001 |
| WO | WO 01/21100 | 3/2001 |
| WO | WO 01/26726 | 4/2001 |
| WO | WO 01/35857 | 5/2001 |
| WO | WO 01/43662 | 6/2001 |
| WO | WO 01/47579 | 7/2001 |
| WO | WO 01/49208 | 7/2001 |
| WO | WO 01/49209 | 7/2001 |
| WO | WO 01/49215 | 7/2001 |
| WO | WO 01/49355 | 7/2001 |
| WO | WO 01/52768 | 7/2001 |
| WO | WO 01/58382 | 8/2001 |
| WO | WO 01/60442 | 8/2001 |
| WO | WO 01/67989 | 9/2001 |
| WO | WO 01/70326 | 9/2001 |
| WO | WO 01/72205 | 10/2001 |
| WO | WO 01 87183 | 11/2001 |
| WO | WO 01/89413 | 11/2001 |
| WO | WO 01/91824 | 12/2001 |
| WO | WO 0222046 | 3/2002 |
| WO | WO 02060519 | 8/2002 |

OTHER PUBLICATIONS

"Endovascular Grafts, Stents Drive Interventional Radiology Growth," *Cardiovascular Device Update*, 2(3):1-12 (Mar. 1996).
"Protruding Atheromas in the Thoracic Aortic and Systemic Embolization," pp. 423-427 American College of Physicians (1991).
"Recognition and Embolic Potential of Intraaortic Atherosclerotic Debris," American College of Cardiology (Jan. 1991).
Cragg, Andrew et al., "A New Percutaneous Vena Cava Filger," *AJR*, 141:601-604 (Sep. 1983).
Cragg, Andrew et al., "Nonsurgical Placement of Arterial Endoprosthesis: A New Technique Using Nitinol Wire," *AJR*, pp. 261-263 (Apr. 1983).
Diethrich et al., "Percutaneous Techniques for Endoluminal Carotid Interventions," *J. Endovasc. Surg.*, 3:182-202 (1996).
Fadali, A. Moneim, "A filtering device for the prevention of particulate embolization during the course of cardiac surgery," *Surgery*, 64(3):634-639 (Sep. 1968).
Haissaguerre et al., "Spontaneous Initiation of Atrial Fibrillation by Ectopic Beats Originating in the Pulmonary Veins," *The New England Journal of Medicine*, 339(10):659-666 (Sep. 1988).
Jordan, Jr. et al.," Microemboli Detected by Transcranial Dopper Monitoring . . . ", Cardiovascular Surgery, 7(1)33-38 (Jan. 1999).
Lesh, "Can Catheter Ablation Cure Atrial Fibrillation?" *ACC Current Journal Review*, pp. 38-40 (Sep./Oct. 1997).
Lund et al., "Long-Term Patentcy of Ductus Arteriosus After Balloon Dilation: an Experimental Study," *Laboratory Investigation*, 69(4):772-774 (Apr. 1984).
Marache et al., "Percutaneous Transluminal Venous Angioplasty . . . ," *American Heart Journal*, 125 (2 Pt 1):362-366 (Feb. 1993).
Mazur et al., "Directional Atherectomy with the Omnicath™: A Unique New Catheter System," *Catheterization and Cardiovascular Diagnosis*, 31:17-84 (1994).
Moussa, MD, Issaam "Stents Don't Require Systemic Anticoagulation . . . But the Technique (and Results) Must be Optimal," *Journal of Invasive Cardiol.*, 8(E):3E-7E, (1996).
Nakanishi et al., "Catheter Intervention to Venous System Using Expandable Metallic Stents," *Rinsho Kyobu Geka*, 14(2):English Abstract Only (Apr. 1994).
Onal et al., "Primary Stenting for Complex Atherosclerotic Plaques in Aortic and Iliac Stenoses," *Cardiovascular &Interventional Radiology*, 21(5):386-392 (1998).
Theron et al., "New Triple Coaxial Catheter System for Carotid Angioplasty with Cerebral Protection," *American Journal of Neuroradiology*, 11:869-874 (1990).
Tunick et al., "Protruding atherosclerotic plaque in the aortic archo f patients with systemic embolization: A new finding seen by transesophageal echocardiography," *American Heart Journal* 120(3):658-600 (Sep. 1990).
Waksman et al., "Distal Embolization is Common After Directional Atherectomy . . . ," American Heart Journal, 129(3):430-435 (1995).
Wholey, Mark H. et al., PTA and Stents in the Treatment of Extracranial Circulation, *The Journal of Invasive Cardiology*, 8(E):25E-30E (1996).

* cited by examiner

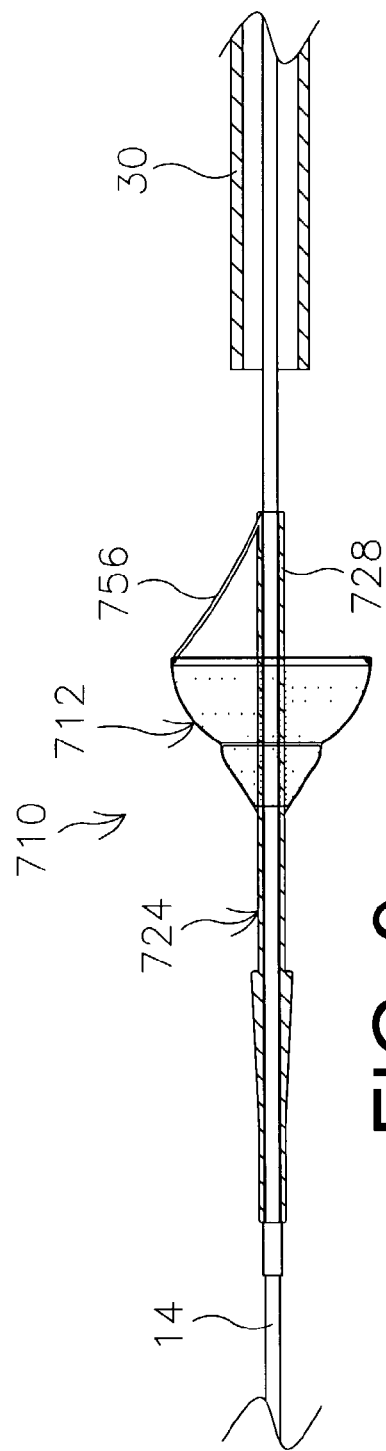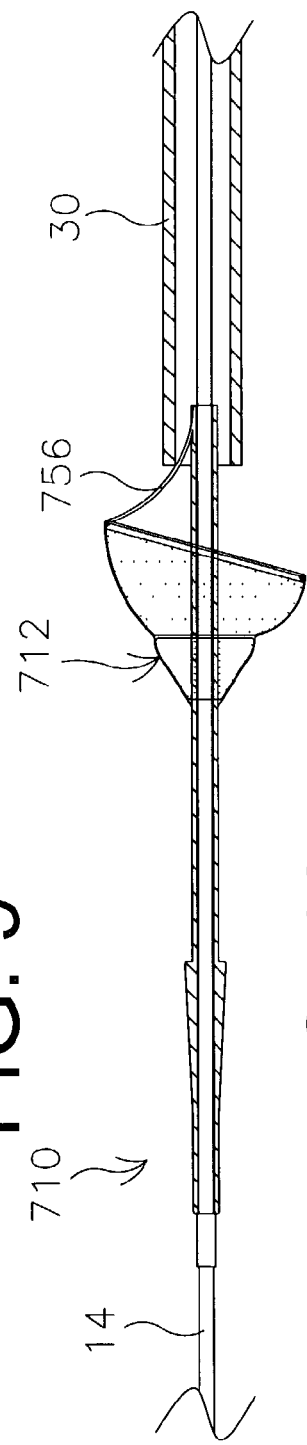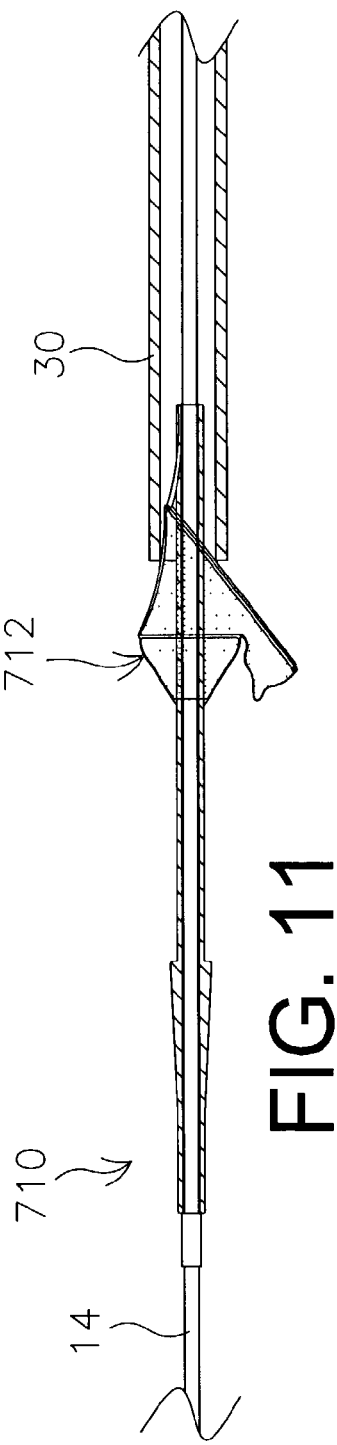

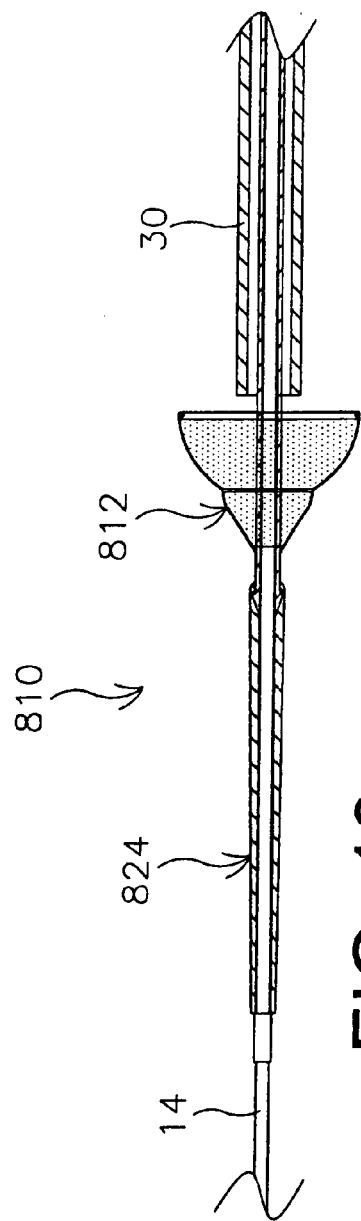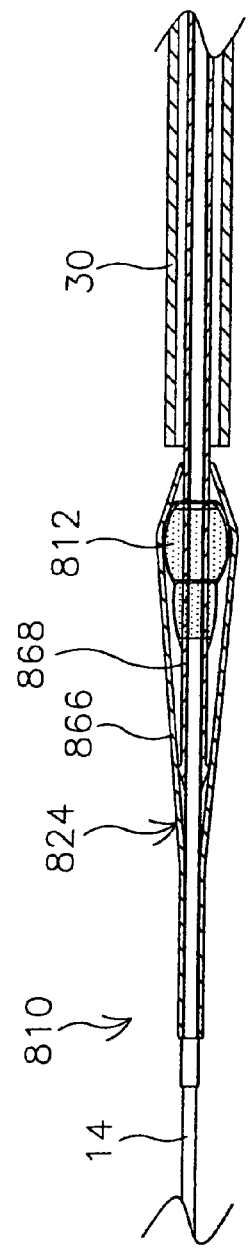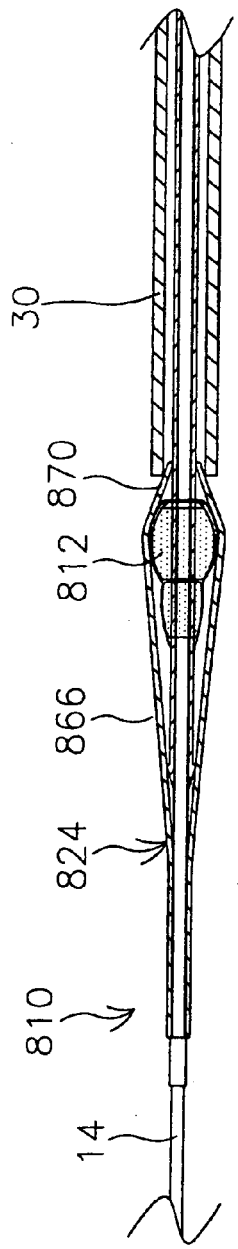

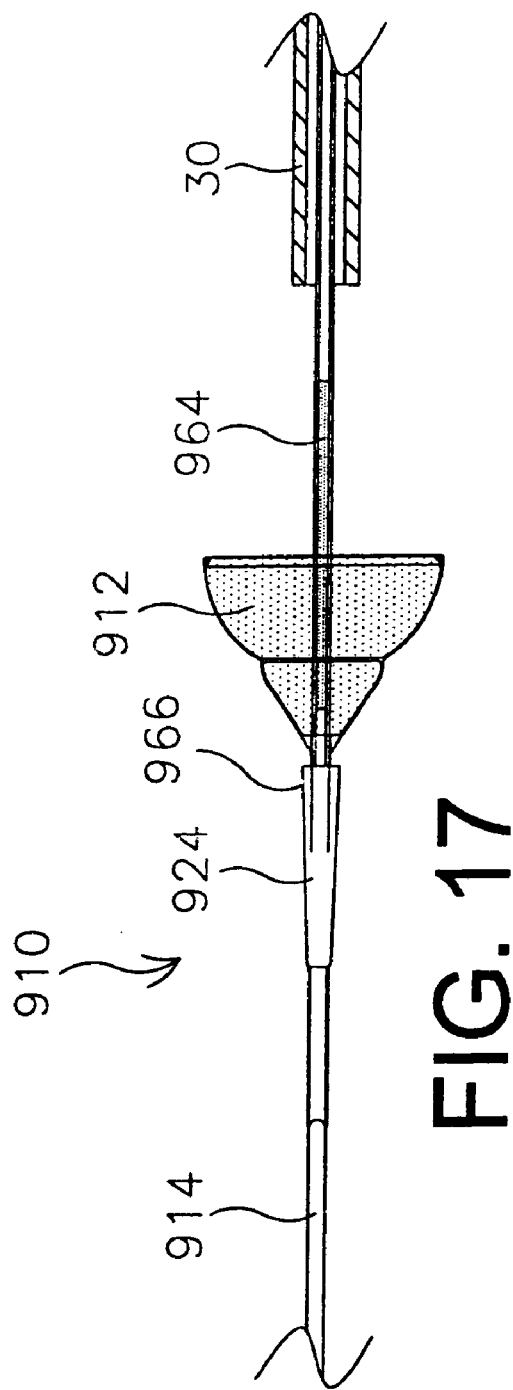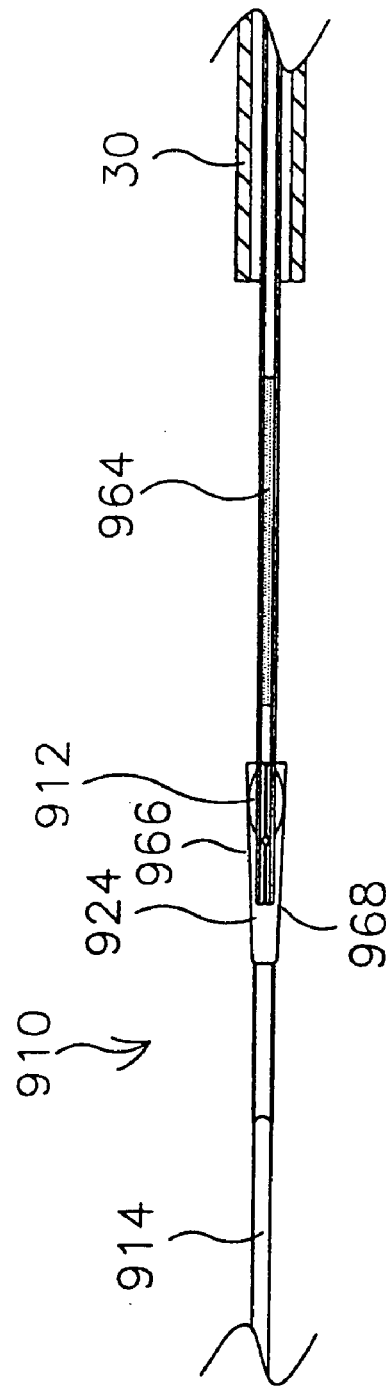

METHOD OF MAKING AN EMBOLIC FILTER

FIELD OF THE INVENTION

The present invention pertains to devices for filtering debris from a body lumen. More particularly, the present invention pertains to devices for filtering embolic debris that is generated by intravascular intervention.

DESCRIPTION OF THE RELATED ART

Heart and vascular disease are majors problem in the United States and throughout the world. Conditions such as atherosclerosis result in blood vessels becoming blocked or narrowed. This blockage can result in lack of oxygenation of the heart, which has significant consequences since the heart muscle must be well oxygenated in order to maintain its blood pumping action.

Occluded, stenotic, or narrowed blood vessels may be treated with a number of relatively non-invasive medical procedures including percutaneous transluminal angioplasty (PTA), percutaneous transluminal coronary angioplasty (PTCA), and atherectomy. Angioplasty techniques typically involve the use of a balloon catheter. The balloon catheter is advanced over a guidewire such that the balloon is positioned adjacent a stenotic lesion. The balloon is then inflated and the restriction of the vessel is opened. During an atherectomy procedure, the stenotic lesion may be mechanically cut away from the blood vessel wall using an atherectomy catheter.

During angioplasty and atherectomy procedures, embolic debris can be separated from the wall of the blood vessel. If this debris enters the circulatory system, it could block other vascular regions including the neural and pulmonary vasculature. During angioplasty procedures, stenotic debris may also break loose due to manipulation of the blood vessel. Because of this debris, a number of devices, termed embolic protection devices, have been developed to filter out this debris.

BRIEF SUMMARY OF THE INVENTION

The present invention relates to embolic protection filters. In some embodiments, the present invention includes an embolic protection filter assembly. The assembly may include a filter coupled to an elongate shaft. The filter may include a number of features. For example, the filter may also include or otherwise be coupled with a distal tip. In some embodiments, the filter (together with the distal the tip) may be slidable over the shaft.

The filter may be delivered to an appropriate location (e.g., adjacent a lesion within a blood vessel) with a delivery catheter. In some embodiments, the filter may be self-expanding so that retracting the delivery catheter from the filter results in the filter expanding. An aspiration tube or other suitable aspiration means may be used to aspirate embolic debris from the filter at any time during the filtering procedure. Upon completing of the intervention, a retrieval catheter or other suitable means may be used to retrieve the filter.

BRIEF DESCRIPTION OF THE DRAWINGS

FIG. 9 is a partial cross-sectional view of another example embolic protection filter assembly that includes a strut;

FIG. 10 is a partial cross-sectional view of an embolic protection filter assembly partially collapsed;

FIG. 11 is a partial cross-sectional view of an embolic protection filter assembly partially collapsed;

FIG. 13 is a partial cross-sectional view of another example embolic protection filter assembly;

FIG. 14 is a partial cross-sectional view of an embolic protection filter assembly collapsed;

FIG. 15 is a partial cross-sectional view of an embolic protection filter assembly collapsed and disposed within a retrieval sheath;

FIG. 17 is a partial cross-sectional view of another example embolic protection filter assembly;

FIG. 18 is a partial cross-sectional view of an embolic protection filter assembly collapsed;

DETAILED DESCRIPTION

Figure 1:
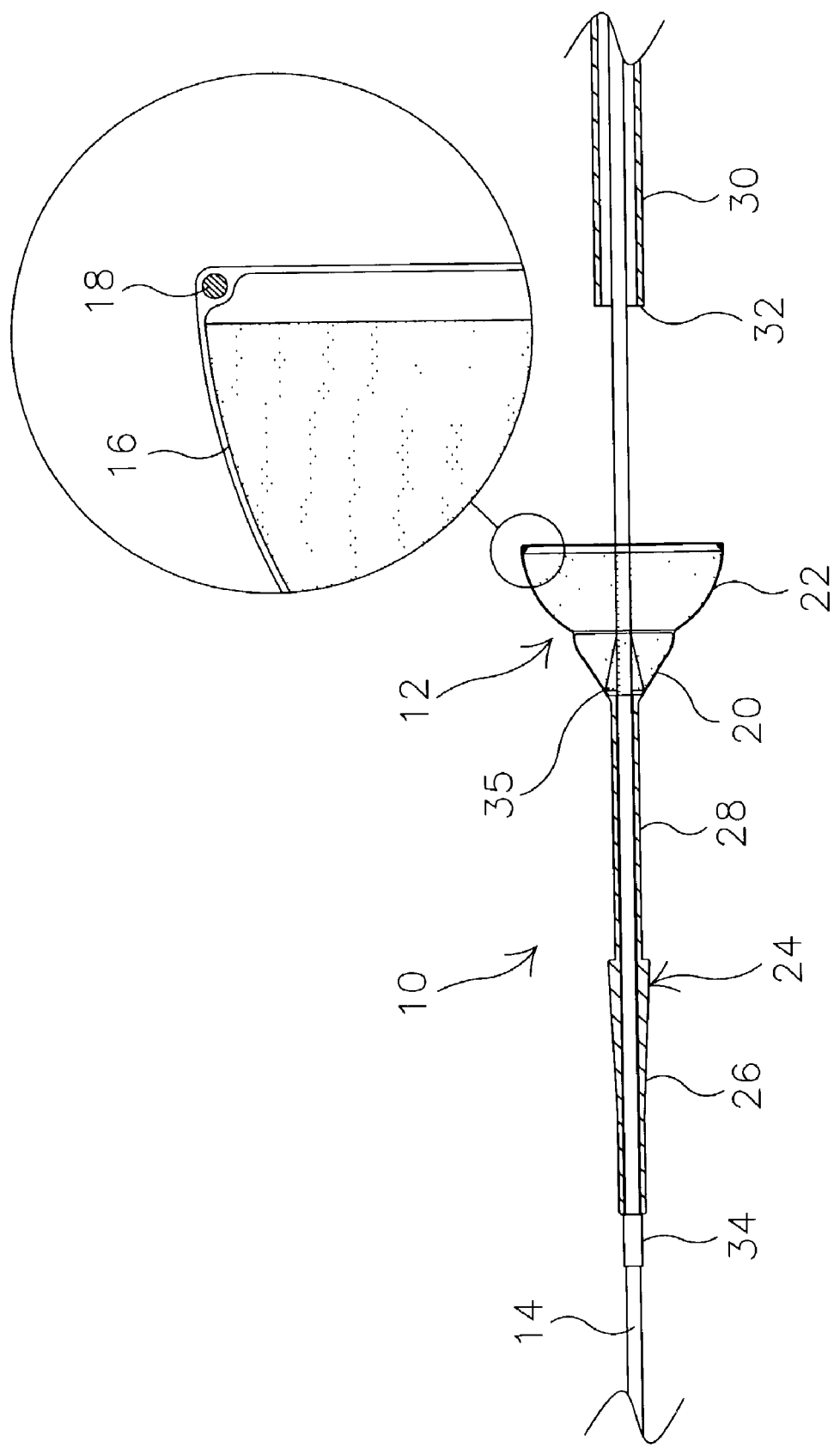
FIG. 1 is a partial cross-sectional view of an embodiment of an embolic protection filter assembly.

The following description should be read with reference to the drawings wherein like reference numerals indicate like elements throughout the several views. The detailed description and drawings illustrate example embodiments of the claimed invention.

FIG. 1 is a partial cross-sectional view of an embodiment of an embolic protection filter assembly 10. Assembly 10 includes an embolic protection filter 12 coupled to an elongate shaft 14. Filter 12 includes an expandable support member 18. Support member 18 may be adapted and configured to shift filter 12 between a first generally collapsed configuration and a second generally expanded configuration to define an open filler month.

Filter 12 may be comprised of a polyurethane nylon sheet, silicone filter or other suitable material. In some embodiments, the filter material may be injection molded over support member 18. The filter material includes at least one opening that may be, for example, formed by laser techniques. The holes or openings are sized to allow blood flow therethrough but restrict flow of debris or emboli floating in the body lumen or cavity. As stated above, filter 12 is adapted to shift between a collapsed configuration and an expanded configuration. In general, the collapsed configuration is appropriate for advancing filter 12 through the vasculature and the expanded configuration is appropriate for collecting debris from the vasculature.

Filter 12 may include distal portion 20 and an enlarged proximal portion 22. Distal portion 20 may be generally tapered. Additionally, filter 12 may include a tapered tip or nose cone 24. Proximal portion may be enlarged so as to increase the filtering capacity of filter 12. Filtering capacity is defined as the amount of embolic material that filter 12 can capture before becoming saturated. This feature may allow multiple embodiments of filter 12 to be constructed that have different filtering capacities.

As stated above, filter 12 may include or otherwise be coupled with tip 24. Tip 24 generally includes a tapered distal region 26 and a proximal region 28 that is coupled to or directly connected to filter 12. Distal region 26 is configured so that when filter 12 is disposed within a delivery catheter 30, the tapered distal region 26 extends from a distal end 32 of delivery catheter 30 to provide it with an atraumatic tip (please see FIG. 2). It can be appreciated that catheter 30 may comprise any number of catheters (diagnostic, therapeutic, or guide) as well as other medical devices and should not be limited to a "delivery" catheter.

In some embodiments, tip 24 is generally tubular and adapted to be slidable over shaft 14. According to this embodiment, filter 12 is connected to tip 24 so that filter 12 can be advanced or "slid" over shaft 14. A number of methods may be used to advance filter 12 over shaft 14. For example, filter 12 may be disposed within delivery catheter 30 and advanced (along with delivery catheter 30) over shaft 14. In this embodiment, filter 12 may have a greater coefficient of friction with delivery catheter 30 than with shaft 14 so that both filter 12 and delivery catheter 30 can be advanced over shaft 14 without filter 12 significantly shifting its position within catheter 30. Alternatively, a pusher or other appropriate physical means may be used to advance filter 12 and tip 24 over shaft 14.

Upon reaching a desired location along shaft 14, it is important to be able to remove delivery catheter 30 so that filter 12 may be delivered (i.e., expanded to essentially appose the blood vessel). In some embodiments, assembly 10 may include a distal stop 34 coupled to shaft 14. Distal stop 34 is sized so that tip 24 may be passed over a portion of stop 34 and then be friction fit thereto. To allow delivery catheter 34 to be removed, it may be beneficial for the coefficient of friction between tip 24 and stop 34 to be greater than that between tip 24 and delivery catheter 30. Thus, tip 24 can fit tightly enough with stop 34 so that catheter 30 can be retracted without significantly altering the position of filter 12.

Additionally, shaft 14 may include a proximal stop 35. Proximal stop 35 is generally tapered (e.g., becomes larger in the distal direction) and allows assembly 10 to pass over (in the distal direction) but limit the ability of assembly 10 to pass back over in the proximal direction. Proximal stop 35 may be used in conjunction with distal stop 34 to define a specific target region along shaft 14 where filter 12 can be disposed. Moreover, proximal stop 35 may also be useful for holding filter 12 in position when retracting catheter 30.

The feature of tip 24 being generally tubular allows filter assembly 10 to be used with essentially any shaft 14. For example shaft 14 may comprise a guidewire, catheter (e.g., a guide, diagnostic, or therapeutic catheter), or other similar medical device. Thus, tip 24 can make assembly 10 very flexible in terms of its utility with a number of differing devices and interventions.

Figure 2:
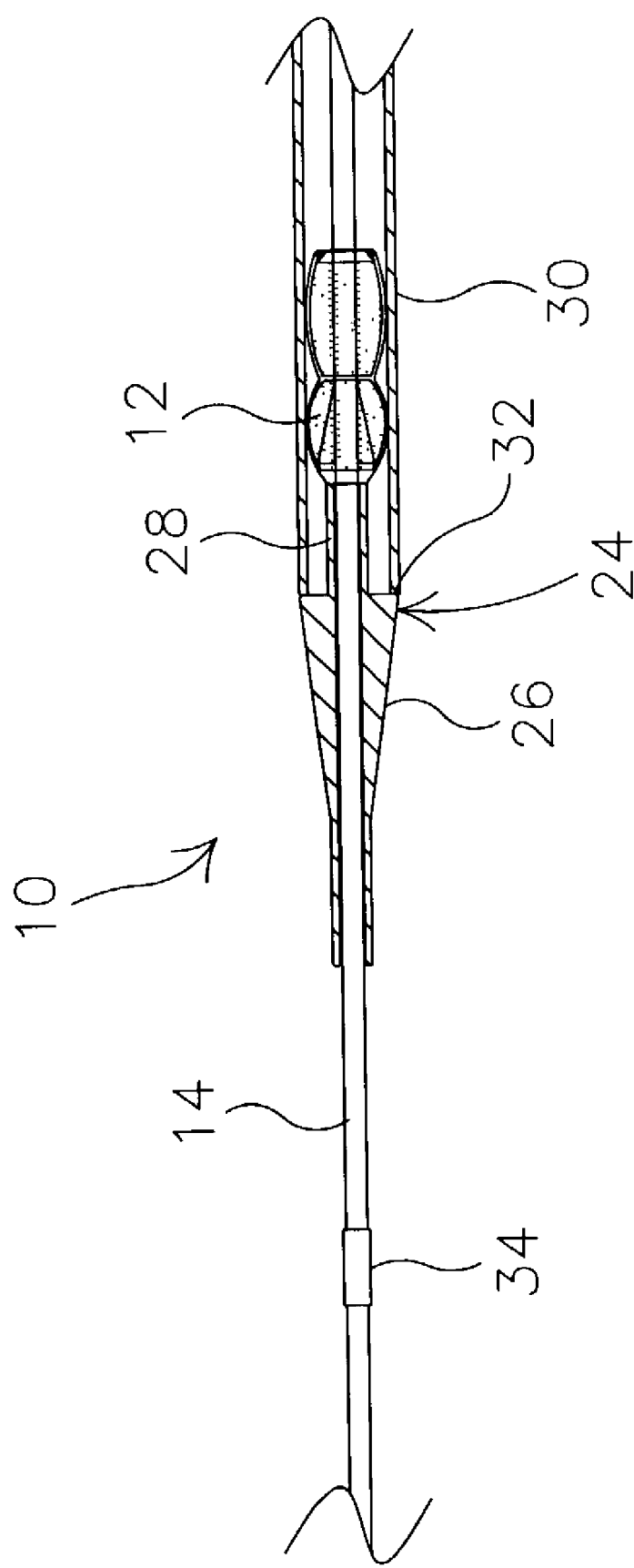
FIG. 2 is a partial cross-sectional view of an embodiment of an embolic protection filter assembly, wherein the filter is collapsed within a delivery catheter.

FIG. 2 is a partial cross-sectional view of assembly 10, wherein filter 12 is collapsed within delivery catheter 30. The configuration shown in FIG. 2 is appropriate for advancing assembly 10 through the vasculature (or other body lumen). As can be seen, assembly 10 can be coupled to delivery catheter 30 such that filter 12 assumes the collapsed configuration within catheter 30 (e.g., by back-loading filter 12 into catheter 30). Also, tip 24 can be configured such that distal region 26 extends from distal end 32 of catheter 30, thus providing an atraumatic tip to assembly 10.

In use, filter 12 (as well as tip 24 and catheter 30) can be advanced over shaft 14 to an area of interest. In some embodiments, filter 12 is advanced distally until tip 24 becomes friction fit or otherwise coupled to stop 34 as described above. Once assembly 10 is advanced to the desired location, catheter 30 can be withdrawn proximally from filter 12 and tip 24. Withdrawing catheter 30 allows filter 12 to shift to the expanded configuration (e.g., by allowing support member 18 to self-expand).

Figure 3:
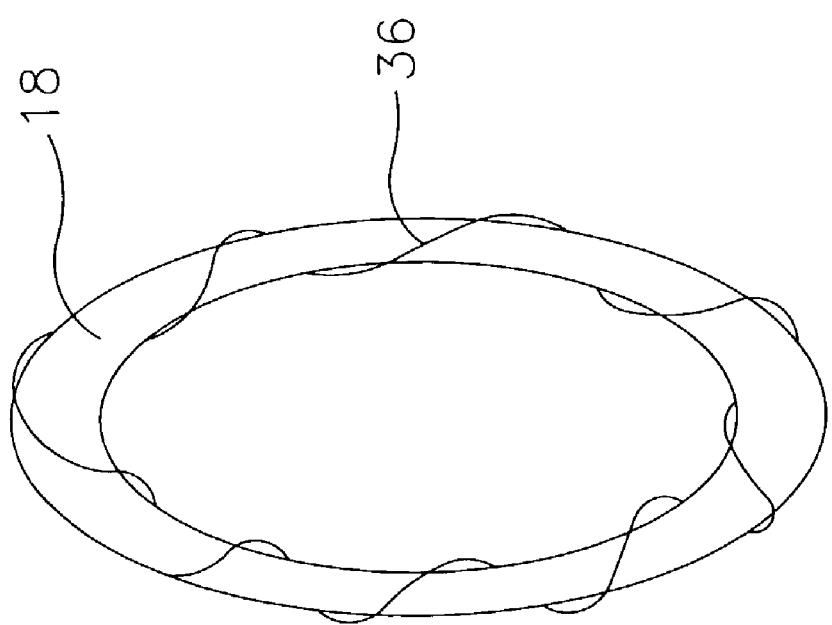
FIG. 3 is a perspective view of an embodiment of a support member for use with an embolic protection filter assembly.

FIG. 3 is a perspective view of an embodiment of support member 18, apart from filter 12. Support member 18 may comprise a ring or loop. In some embodiments, it may be useful to incorporate the property of super-elasticity into support member 18. For example, support member 18 may be comprised of a shape-memory and/or super-elastic alloy such as nickel-titanium alloy. The super-elasticity and/or shape memory properties can be used to bias support member into the (second) expanded configuration. Thus, support member 18 will cause filter 12 to self-expand when becoming unconfined by, for example, catheter 30.

A coil or wire 36 may be disposed about support member 18. In some embodiments, wire 36 may be comprised of or include a coating or plating of radiopaque material. Radiopaque materials are understood to be materials capable of producing a relatively bright image on a fluoroscopy screen or another imaging technique during a medical procedure. This relatively bright image aids the user of assembly 10 (and filter 12) in determining its location. Radiopaque materials can include, but are not limited to, gold, platinum, palladium, tantalum, tungsten alloy, plastic material loaded with a radiopaque filler, etc.

Figure 4:
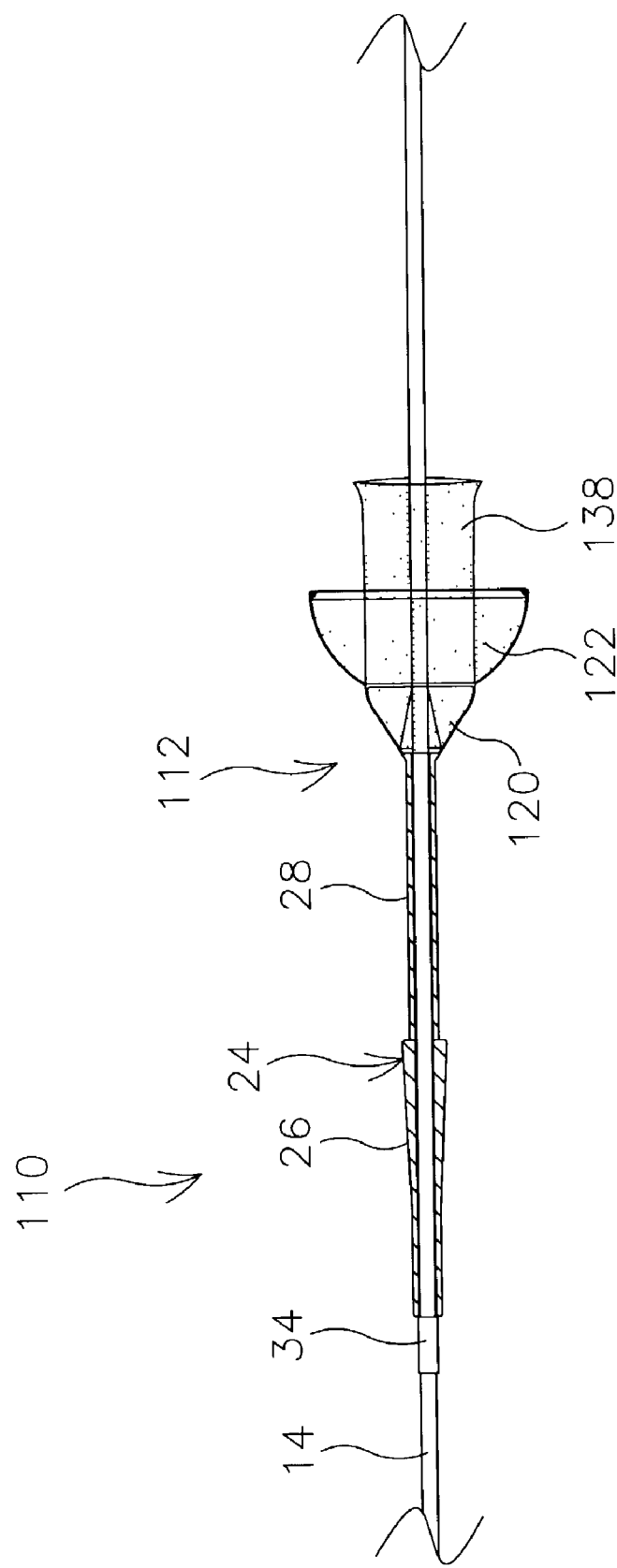
FIG. 4 is a partial cross-sectional view of an alternate embodiment of an embolic protection filter assembly.

FIG. 4 is a partial cross-sectional view of an alternate embodiment of embolic protection filter assembly 110. Assembly 110 is essentially the same in form and function as assembly 10 except that filter 112 includes a narrow proximal portion 138 in addition to distal portion 120 and enlarged proximal portion 122. Because embolic debris can tend to accumulate near distal portion 120, it may be desirable to increase the filtering capacity of distal portion 120. Narrow proximal portion 138 accomplishes this by providing additional surface area to distal portion 120. Thus, narrow proximal portion 138 may be described as being an extension of distal portion 120. In some embodiments, narrow proximal portion 138 extends proximally of portion 122. It can be appreciated that the length of narrow proximal portion 138 can be altered to suit multiple embodiments without departing from the scope of the invention.

Narrow proximal portion 138 may also include a support member (not shown) that functions essentially the same as support member 18. According to this embodiment, narrow proximal portion 138 can be adapted to shift between expanded and collapsed configurations. Alternatively, narrow proximal portion 138 may include an expanding frame or be otherwise self-expanding.

Figure 5:
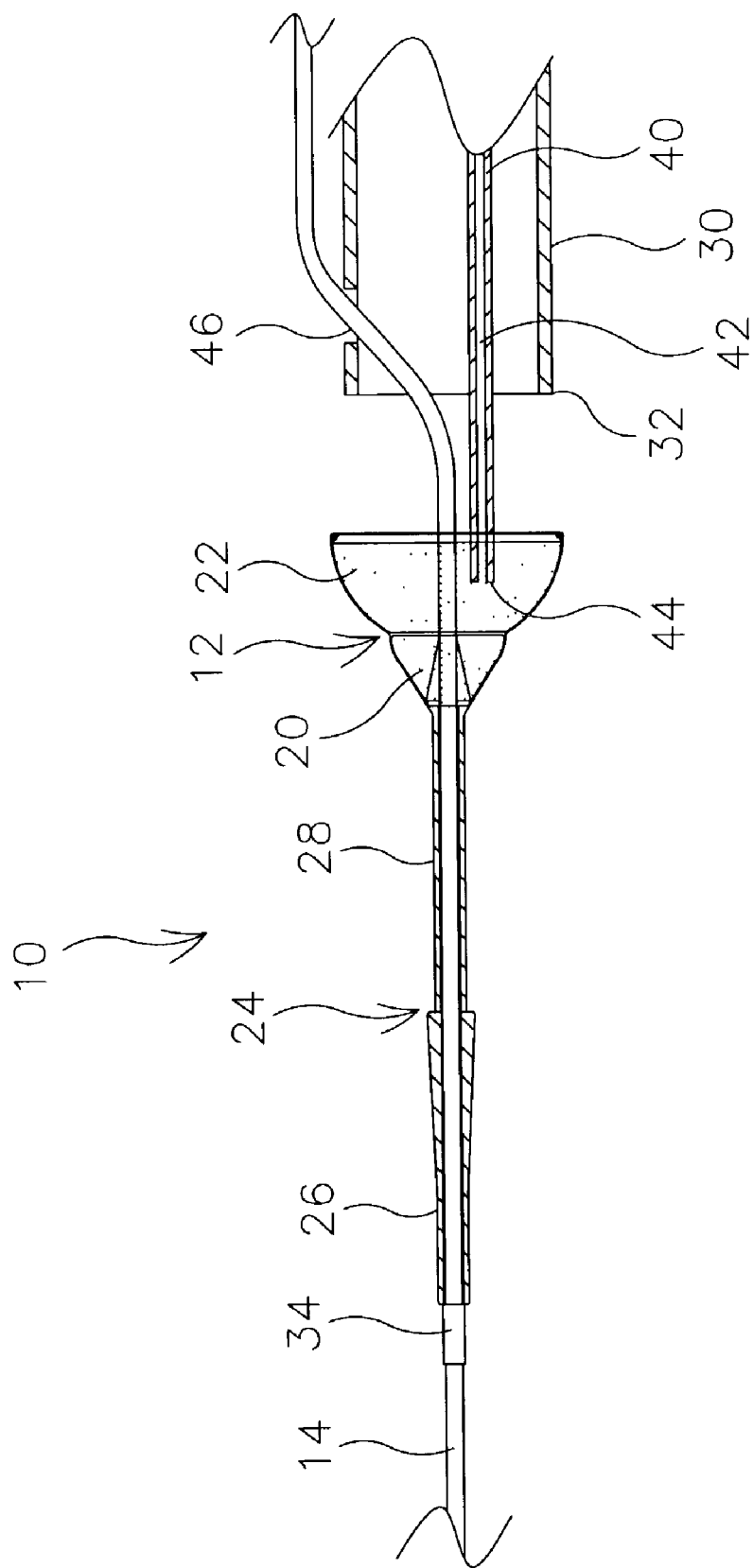
FIG. 5 is a partial cross-sectional view of an embolic protection filter assembly including an aspiration tube.

For several reasons, it may be desirable to aspirate captured embolic debris from filter 12 during an intervention. For example, filter 12 may become saturated with debris and begin to occlude blood flow through a blood vessel. FIG. 5 is a partial cross-sectional view of embolic protection filter assembly 10 further comprising an aspiration tube 40. Aspiration tube 40 includes an aspiration lumen 42 and a distal end 44. Aspiration tube 40 may advanced, for example through catheter 30, to a location near filter 12. Application of a vacuum to aspiration tube 40 allows debris to be aspirated from filter 12 through lumen 42.

Aspiration tube 40 may be used by advancing it within catheter 30 (e.g., through a lumen within catheter 30) until distal end 44 is at least partially disposed adjacent filter 12. In some embodiments, distal end 44 extends within a substantial portion of filter 12 so that embolic debris can be aspirated from a significant portion thereof.

FIG. 5 also illustrates that catheter 30 may include a port 46 adapted to allow single-operator-exchanges of medical devices over shaft 14. This feature may be essentially the same as other analogous single-operator-exchange medical devices.

Figure 6:
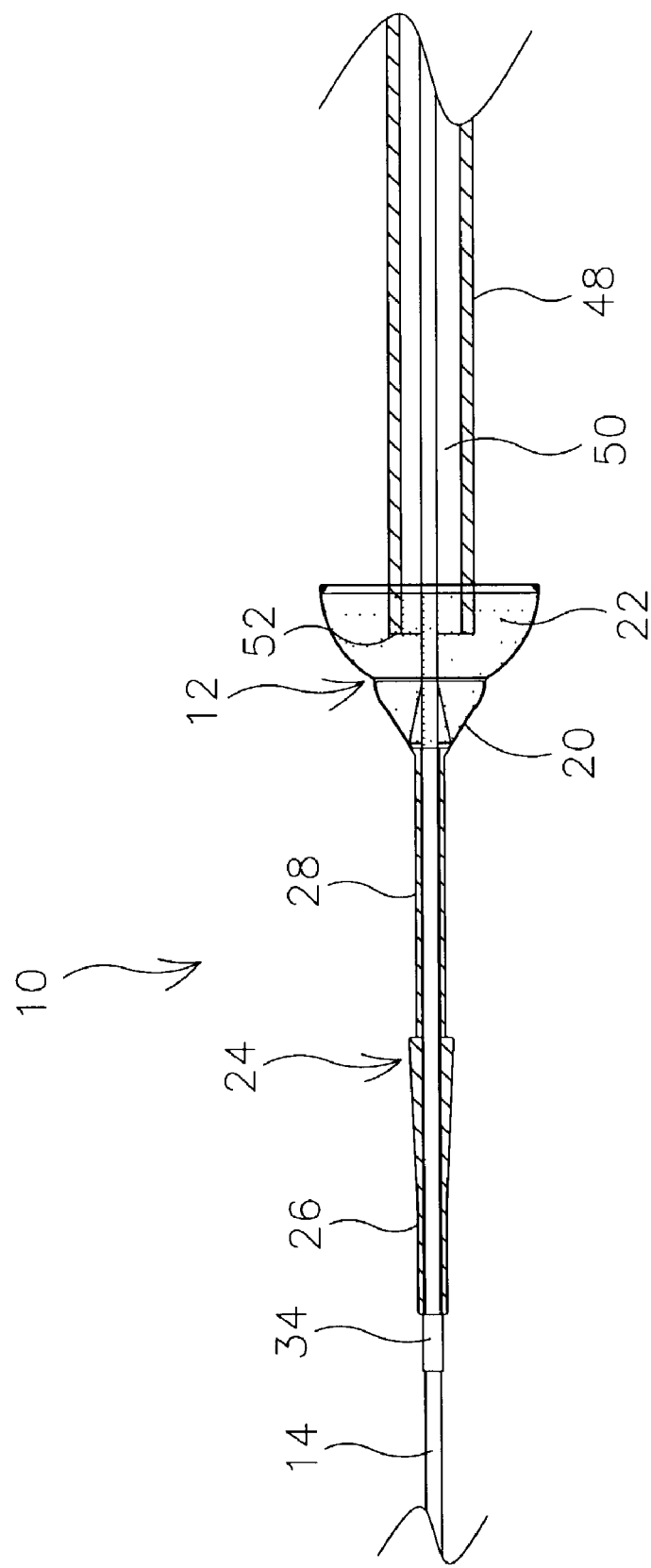
FIG. 6 is a partial cross-sectional view of an embolic protection filter assembly including an alternative aspiration tube.

FIG. 6 is a partial cross-sectional view of embolic protection filter assembly 10 further comprising an alternative aspiration tube 48. Tube 48 is essentially the same in form and function as tube 40 and includes an aspiration lumen 50 and a distal end 52. In some embodiments, tube 48 is delivery catheter 30 or can be used in place of catheter 30. Alternatively, tube 48 can be advanced over shaft 14 independently of delivery catheter 30.

Figure 7:
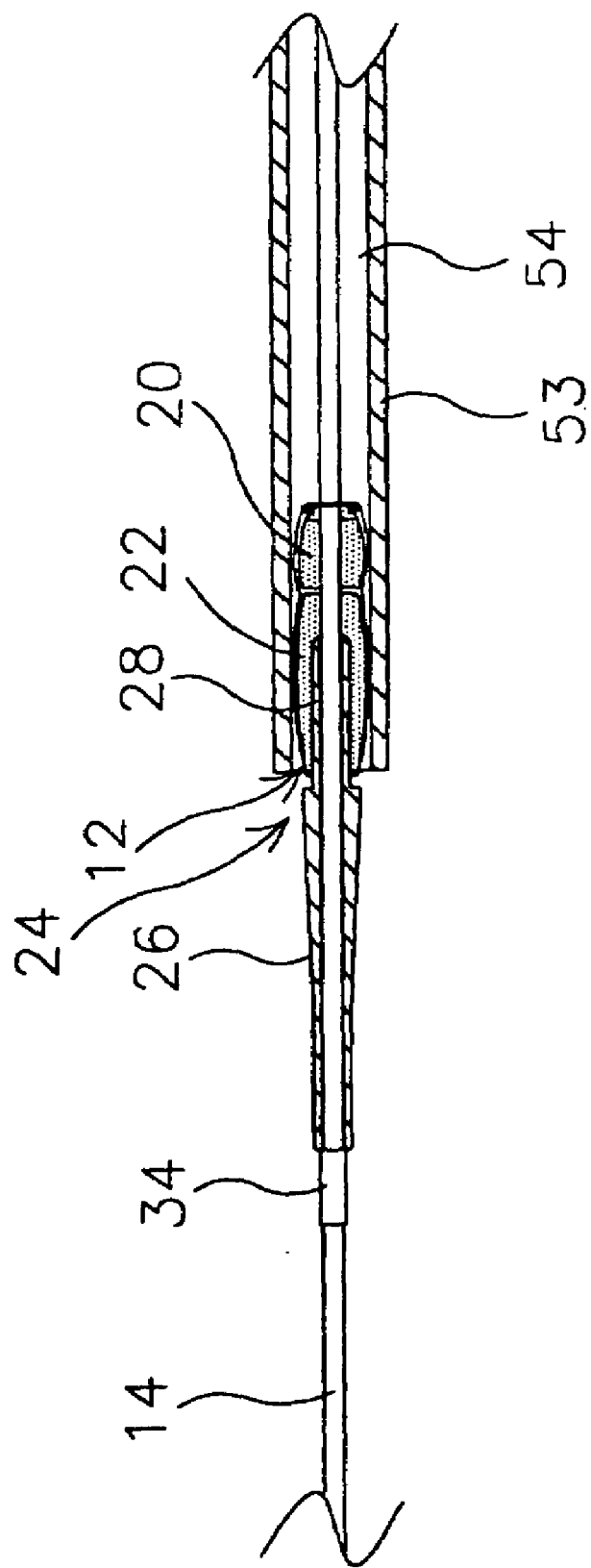
FIG. 7 is a partial cross-sectional view of an embolic protection filter assembly wherein an aspiration tube is advanced over the filter, prolapsing the filter.

After an intervention is complete, assembly 10 can be retrieved from the vasculature. FIG. 7 illustrates an embodiment suitable for retrieval wherein a tube 53 is advanced over filter 12, prolapsing filter 12. Tube 53 may comprise a retrieval catheter, an aspiration tube (e.g., tube 40 or 48), delivery catheter 30, or any other suitable tube.

Tube 53 can be advanced over shaft 14 in the distal direction until encountering filter 12. Tube 53 can then be further advanced so as to prolapse filter 12. When prolapsed, filter 12 generally becomes disposed over proximal portion 28 of tip 24. Tube 53 can then be advanced over filter 12. Prolapsing filter 12 places filter 12 in a collapsed configuration suitable for removal from the vasculature. Because filter 12 may contain embolic debris and because prolapsing filter 12 may cause the debris to disassociate from filter 12, it may be beneficial to apply a vacuum to tube 53 in order to aspirate debris from filter 12 before, during, and after prolapsing filter 12.

Figure 8:
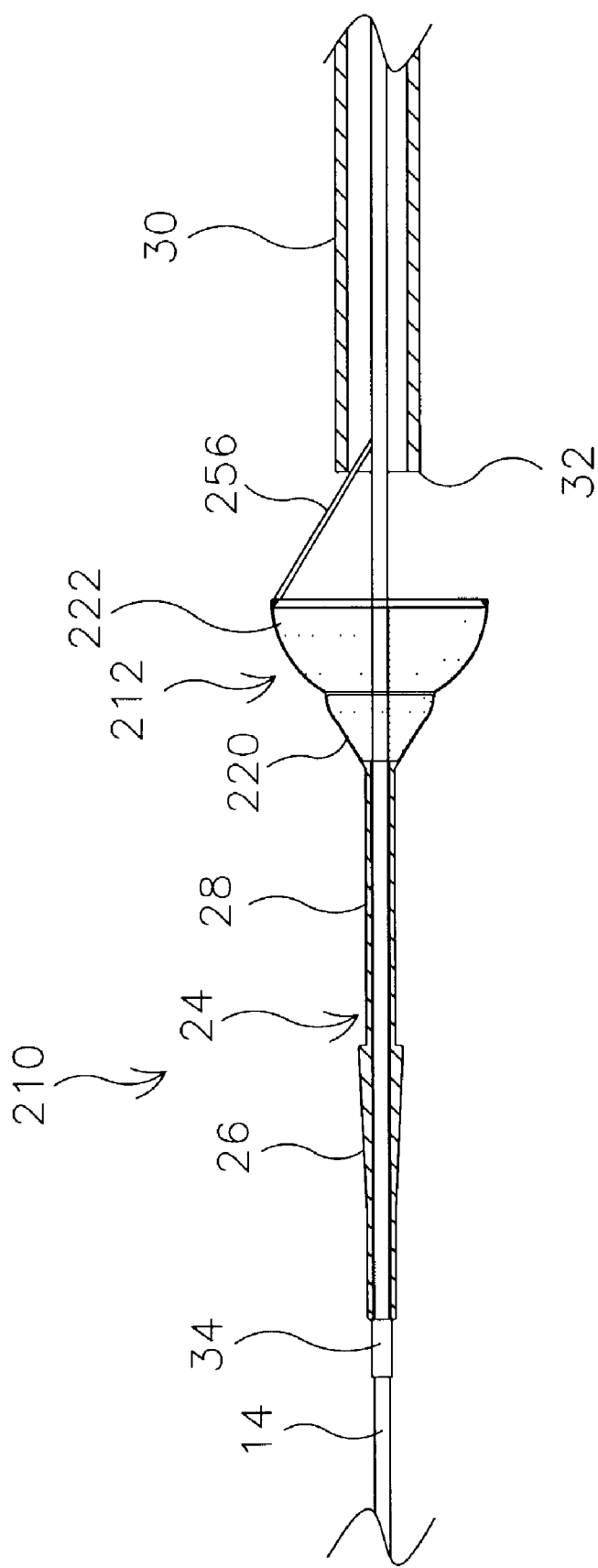
FIG. 8 is a partial cross-sectional view of an embolic protection filter assembly wherein the filter includes a strut.
Figure 12:
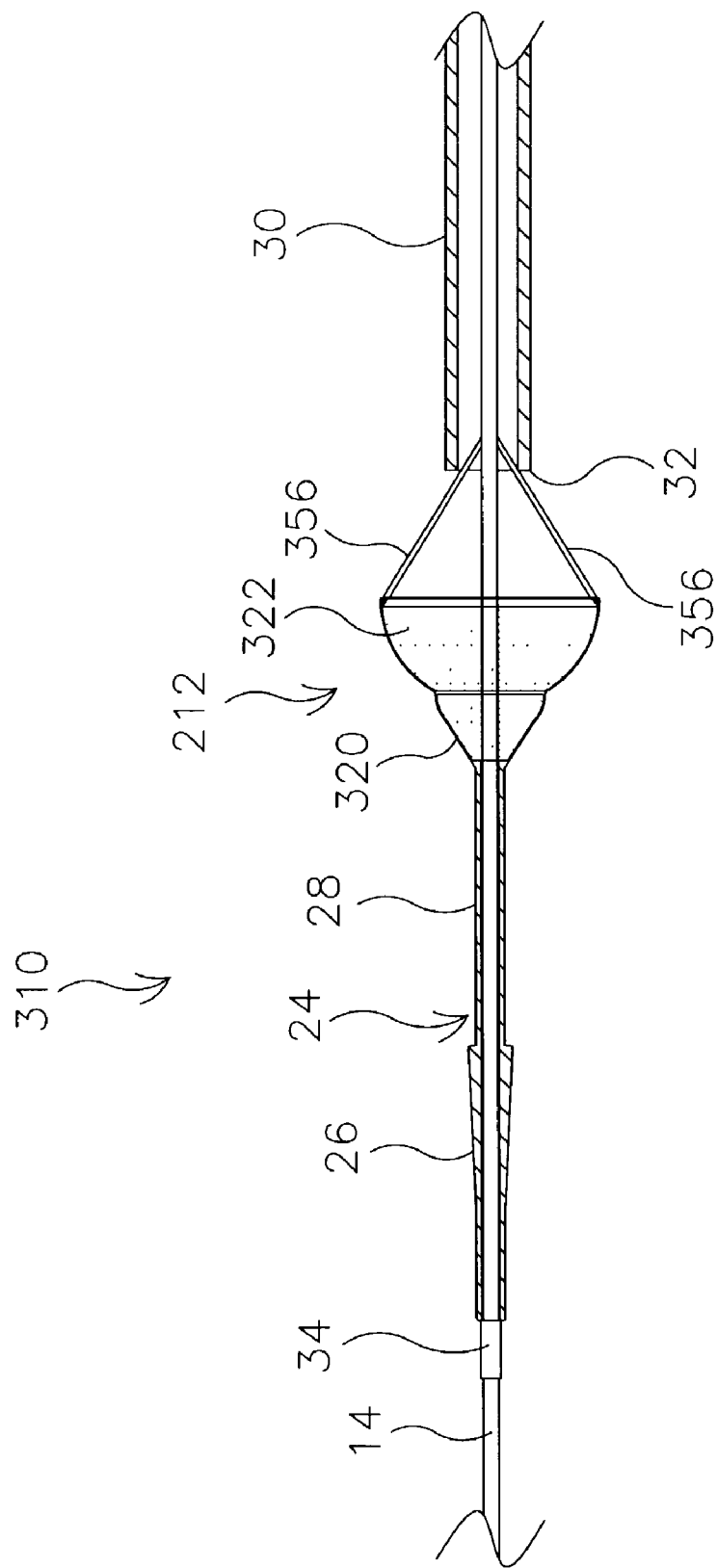
FIG. 12 is a partial cross-sectional view of an embolic protection filter assembly wherein the filter includes more than one strut.

FIG. 8 is a partial cross-sectional view of embolic protection filter assembly 210. Assembly 210 is essentially the same in form and function as assembly 10, except that filter 212 includes a strut 256 extending between proximal portion 222 and shaft 14. Filter 212 is essentially the same as filter 12 and includes distal portion 220. Strut 256 may allow a catheter or other retrieval device (e.g., catheter 30) to at least partially collapse filter 212 so that it may be disposed within the retrieval catheter. For example, when distal end 32 of catheter 30 is moved in the distal direction distal end 32 may engage strut 256. The result of this engagement is filter 212 tending to shift to the collapsed configuration.

FIG. 9 is a partial cross-sectional view of another example embolic protection filter assembly 710 that illustrates that strut 756, in addition to being coupled to shaft 14, could also be coupled to tip 724. Assembly 710 is essentially the same in form and function as assembly 210 except that proximal portion 728 of tip 724 extends proximally of filter 712 and strut 756 is coupled to proximal portion 728.

FIG. 10 is a partial cross-sectional view of embolic protection filter assembly 710 partially collapsed for retrieval from a body lumen. As sheath 30 is advanced over shaft 14, it engages strut 756. This engagement causes strut 756 to shift in position and begin to shift filter 712 from the expanded configuration toward the collapsed configuration. Further advancement of sheath 30 results in further collapsing of filter 712 as shown in FIG. 11 and, eventually, the substantial (and/or complete) containment of filter 712 within sheath 30 (see, for example, FIG. 7).

Similar to FIGS. 8–11, FIG. 12 illustrates embolic protection filter assembly 310 having more than one strut 356 extending between filter 312 and shaft 14. Filter 312 is essentially the same as filter 12 and includes distal portion 320 and proximal portion 322. Struts 356 function essentially the same as struts 256 and, thus, may be used to collapse and/or retrieve filter 312. It can be appreciated that struts 356 could also be coupled to other parts of assembly 310.

FIG. 13 is a partial cross-sectional view of another example embolic protection filter assembly 810. Assembly 810 is essentially the same in form and function as other assemblies described herein except that it includes an expandable tip 824. Expandable tip 824 is configured so that at least a portion thereof can shift between a generally collapsed configuration (as best seen in FIG. 13) and a generally expanded configuration (as best seen in FIGS. 14 and 15). When tip 824 is expanded, filter 812 may become at least partially collapsed and disposed therein. Thus, expandable tip 824 may be used to aid retrieval of filter 812.

FIG. 14 is a partial cross-sectional view of embolic protection filter assembly 810 with tip 824 in a generally expanded configuration and with filter 812 disposed within tip 824. In order for filter 812 to become disposed within tip 824, sheath 30, for example, may be advanced over shaft 14 to a position adjacent filter 812. Sheath 30 can then be further advanced distally so that it contacts and exerts a force upon filter 812 that is sufficient to slide filter 812 into tip 824. It can be appreciated that other devices may be used to shift filter 812 so that it becomes disposed within tip 824. For example, a pusher tube may be advanced over shaft 14 or within sheath 30 may be used. Additionally, filter 812 may included a reinforced pushing surface that is configured to provide structural support at the point of contact between sheath 30 and filter 812. This surface may be defined by a larger or stronger portion of filter 812, a subassembly disposed adjacent filter 812, a part of the filter frame, and the like.

To assist the shifting of filter 812 between the expanded configuration and the collapsed configuration, tip 824 may include a longitudinal portion 866 and a slidable subassembly 868. Subassembly 868 is connected to filter 812 and may comprise a tube slidably disposed about longitudinal portion 866. According to this embodiment, as filter 812 is shifted distally, subassembly 868 shifts distally along longitudinal portion 866 and filter 812 becomes disposed within tip 824.

As filter 812 becomes at least partially disposed within tip 824, sheath 30 may be advanced distally toward tip 824 so that a proximal bent portion 870 thereof becomes disposed within sheath 30 as shown in FIG. 15. In this configuration, filter 812 can be removed from the body lumen by retracting shaft 14 and sheath 30.

Figure 16:
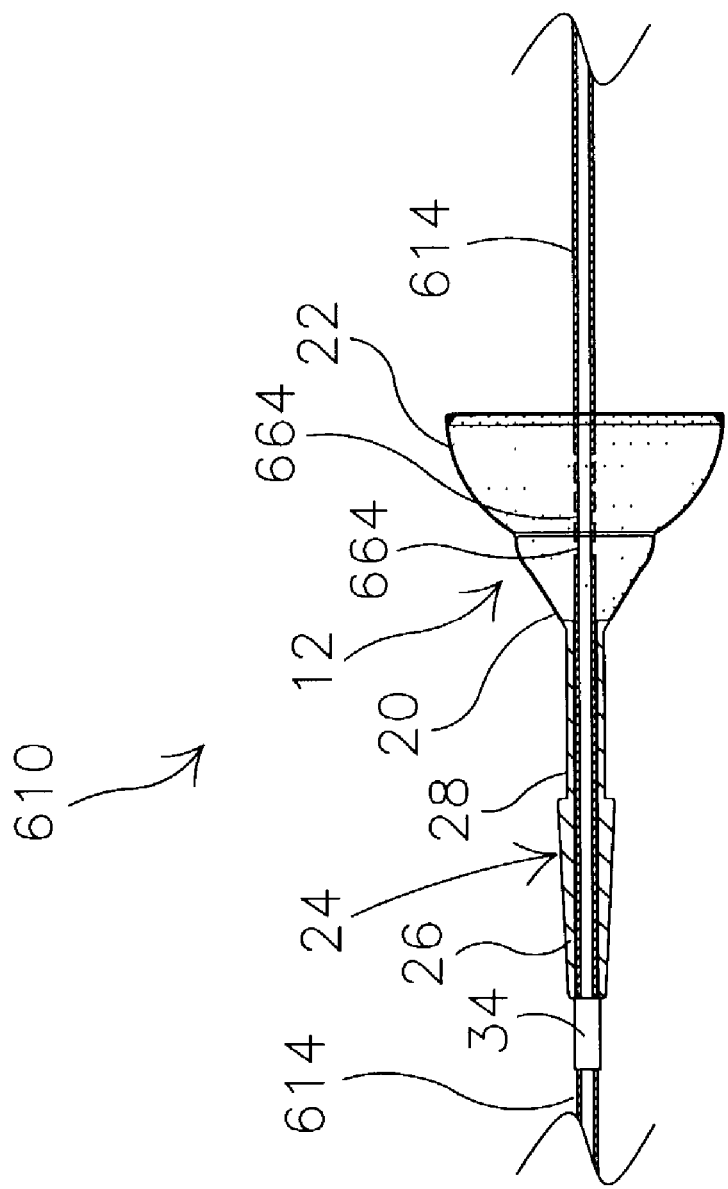
FIG. 16 is a partial cross-sectional view of an embolic protection filter assembly.

FIG. 16 is a partial cross-section view of embolic protection filter assembly 610. Assembly 610 is essentially the same in form and function as assembly 10 except that shaft 614 is tubular and includes one or more aspiration holes 664. In at least some embodiments, shaft 614 has an outside diameter that is comparable to typical guidewires. For example, the outside diameter may be about 0.016 inches or less. Generally, when filter 12 is in a position relative to shaft 614 that is appropriate for filtering embolic debris, holes 664 are located near or within filter 12 so that captured embolic debris may be aspirated through shaft 612.

FIG. 17 is a partial cross-sectional view of another example embolic protection filter assembly 910 that is essentially the same in form and function as assembly 610, except that it includes an expandable tip 924 that functions essentially the same as tip 824. Similar to what is described above, shaft 914 is tubular and includes one or more aspiration holes 964 that can be used to aspirate embolic debris from filter 912 when a vacuum source is connected to the proximal end of shaft 914.

Retrieval of filter 912 may include distally advancing sheath 30 (or another suitable structure) along shaft 914 and exerting force upon filter 912 so that filter 912 becomes at least partially disposed within tip 924 as shown in FIG. 18. The mechanism for shifting filter 912 is essentially the same as what is described above and shown in FIGS. 13–15. For example, tip 924 may include longitudinal portion 966 and subassembly 968 and subassembly may slide distally along longitudinal portion 966.

Figure 19:
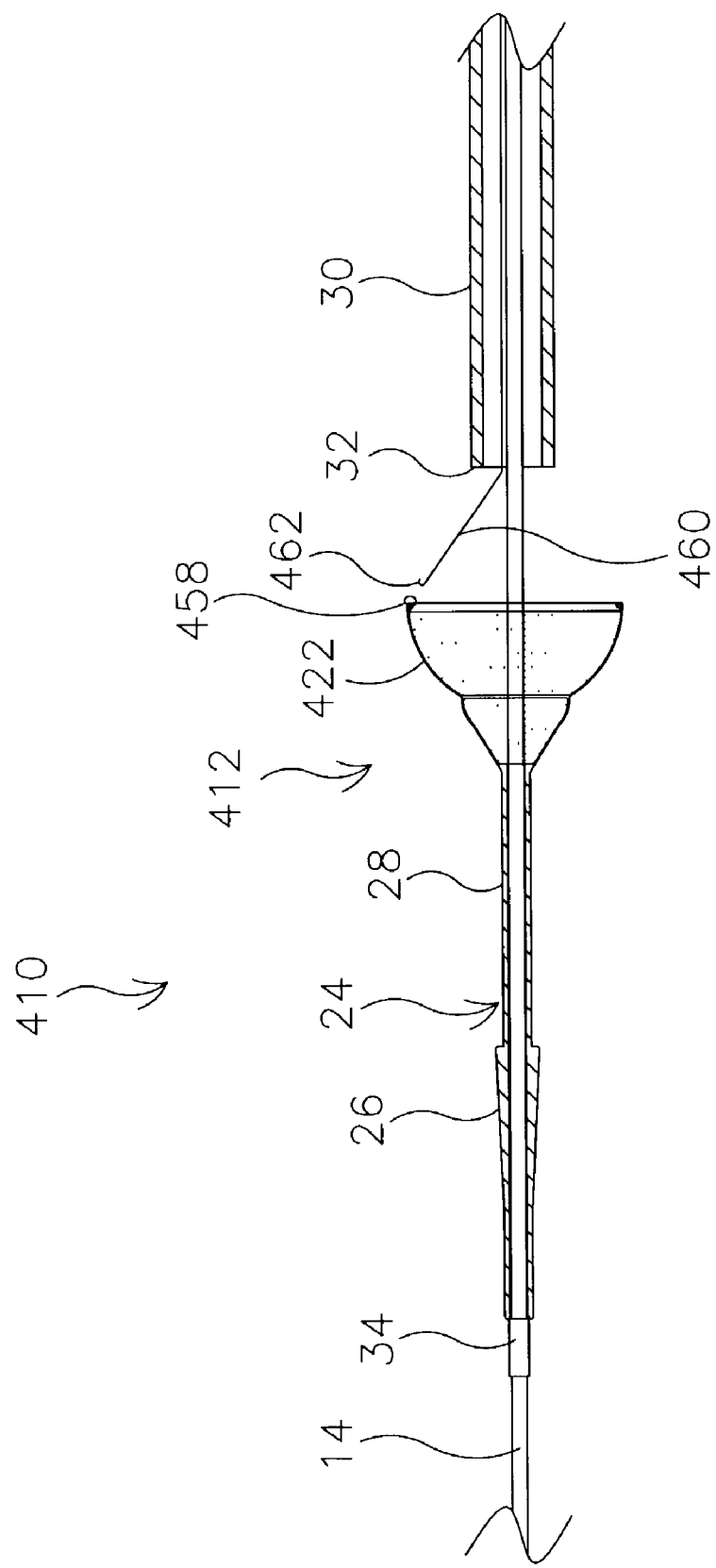
FIG. 19 is a partial cross-sectional view of an embolic protection filter assembly wherein the filter includes pull cord for collapsing the filter.

FIG. 19 is a partial cross-sectional view of embolic protection filter assembly 410. Assembly 410 and filter 412 are essentially the same in form and function as assembly 10 and filter 12, respectively, except that filter 412 includes an engageable ring 458. Engagable ring 458 may be, for example, formed at one end of support member 18 or be connected to a wire or cord disposed about proximal portion 422. Actuating or "pulling" ring 458 results in the circumference of proximal portion 422 becoming smaller. Thus, ring 458 can be used to at least partially collapse filter 412 for retrieval.

Figure 20:
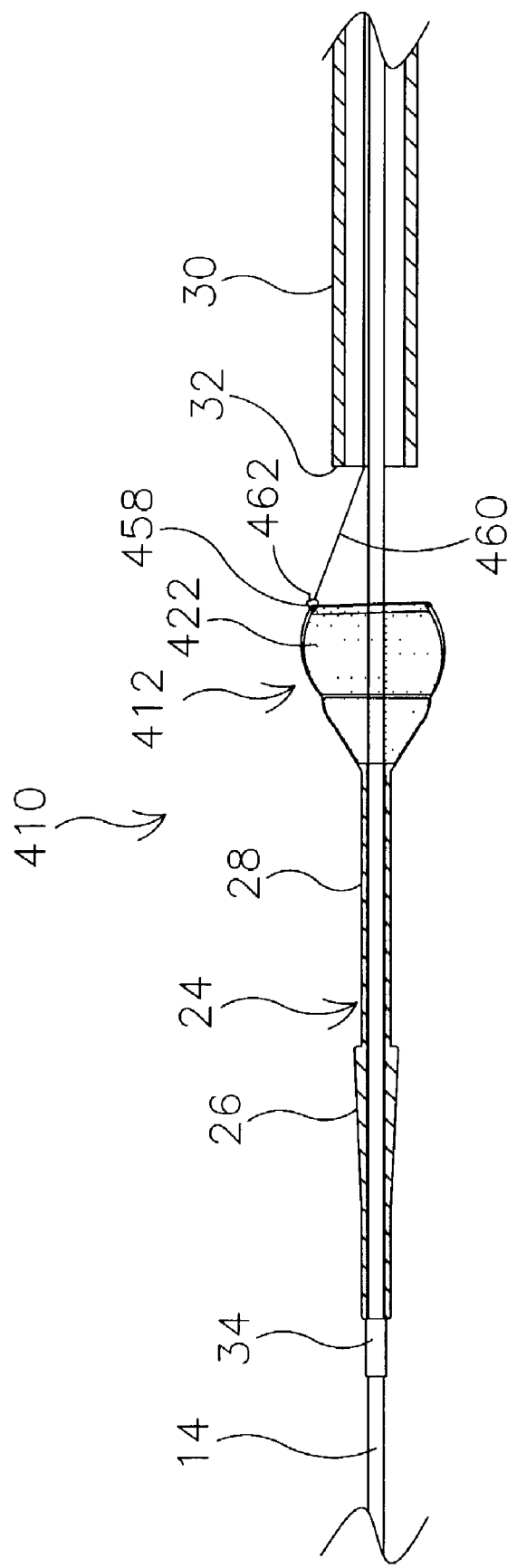
FIG. 20 is a partial cross-sectional view of an embolic protection filter assembly wherein the pull cord is actuated and the filter is partially collapsed.

In some embodiments, ring 458 may be actuated by a pull cord 460. Pull cord 460 may extend distally through catheter 30 and extend out of distal end 32 thereof. To engage ring 458, pull cord may include a distal hook 462 adapted and configured to engage ring 458. According to this embodiment, pull cord 462 can be advanced out of distal end 32 of catheter 30, become engaged with ring 458, and be pulled proximally to collapse filter 412. FIG. 20 illustrates assembly 410 with pull cord 462 engaged with ring 458 and pulled proximally to partially collapse filter 412.

Figure 21:
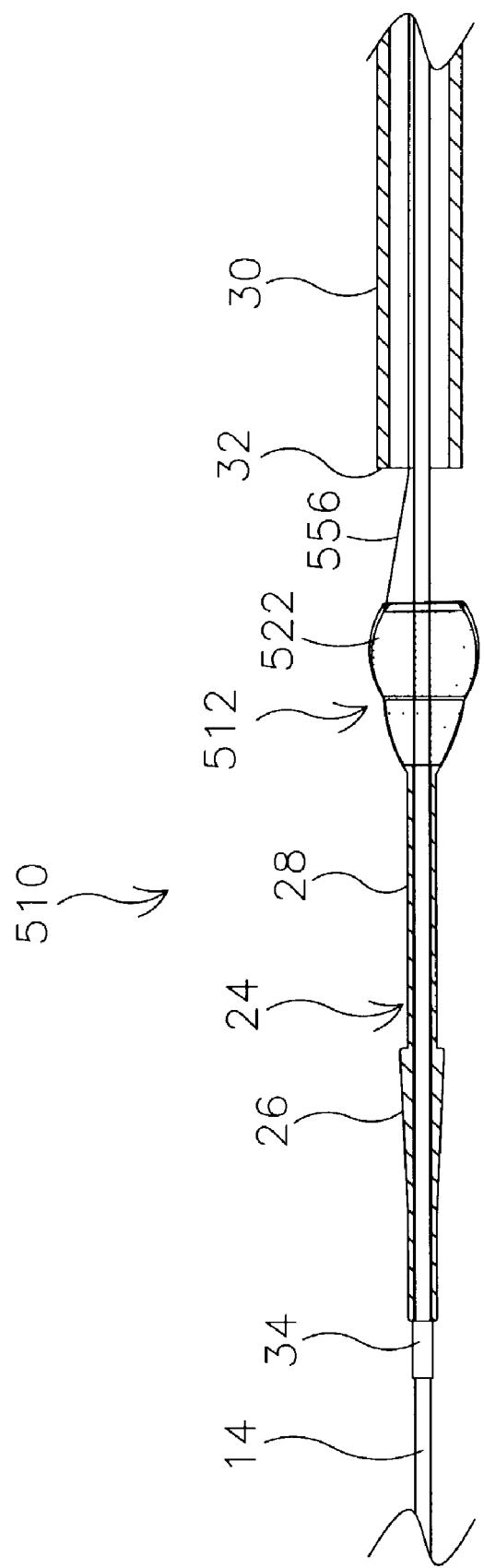
FIG. 21 is a partial cross-sectional view of an embolic protection filter assembly wherein an alternative pull cord is actuated and the filter is partially collapsed.

FIG. 21 is a partial cross-sectional view of embolic protection filter assembly 510 having an alternative pull cord 556. Assembly 510 and filter 512 are essentially the same as assembly 10 and filter 12, respectively. Pull cord 556 is connected to proximal portion 522 of filter 512 such that pull cord 556 can be pulled in the proximal direction to collapse filter 512. In some embodiments, pull cord 556 may comprise an extension or be connected to support member 18. Alternatively, pull cord 556 may be generally disposed about proximal portion 522 so that pulling pull cord 556 tightens or shortens the circumference of proximal portion 522 (and generally the circumference of filter 512) so that filter 512 may be retrieved by catheter 30.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A method of making a device for filtering embolic debris from a body lumen, the method comprising the steps of:
   forming a filter assembly by an injection molding process, the filter assembly including a distal tip and a filter portion;
   forming a plurality of apertures; and
   by the injection molding process wherein the support member is,
   coupling a support member to the filter assembly adapted to shift the filter portion between a first generally collapsed configuration and a second generally expanded configuration.

2. The method in accordance with claim 1, wherein the filter assembly is molded from a filter material comprised of silicon.

3. The method in accordance with claim 1, wherein the support member is comprised of nickel-titanium alloy.

4. The method in accordance with claim 1, wherein the support member further comprises a radiopaque coil disposed about at least a portion of the support member.

5. The method in accordance with claim 1, further comprising the steps of providing an elongate shaft having a proximal end and a distal end, and coupling the filter assembly to the shaft.

6. The method in accordance with claim 5, wherein the shaft is generally tubular and includes plurality of aspiration holes.

7. The method in accordance with claim 5, further comprising the step of slidably disposing an aspiration tube over the shaft.

8. The method in accordance with claim 5, further comprising the step of disposing a distal stop located proximate the distal end of the shaft.

9. The method in accordance with claim 5, further comprising the step of disposing a proximal stop on the shaft.

10. The method in accordance with claim 1, wherein the support member is coupled to the filter assembly by molding the filter assembly to the support member.

11. The method in accordance with claim 1, wherein the plurality of apertures are formed by laser drilling.

12. The method in accordance with claim 1, wherein the filter assembly includes one or more struts.

13. The method in accordance with claim 1, wherein the support member is biased to shift the filter portion into the second generally expanded configuration.

14. The method in accordance with claim 1, further comprising the step of coupling a ring to the filter assembly.

15. The method in accordance with claim 14, further comprising the step of providing a pull cord having a distal hook adapted for engaging the ring.

* * * * *